(12) United States Patent
Dennis

(10) Patent No.: US 7,713,276 B2
(45) Date of Patent: May 11, 2010

(54) OCCLUSION CLIP

(75) Inventor: William G. Dennis, Jacksonville, FL (US)

(73) Assignee: Microline Surgical, Inc., Beverly, MA (US)

( * ) Notice: Subject to any disclaimer, the term of this patent is extended or adjusted under 35 U.S.C. 154(b) by 1574 days.

(21) Appl. No.: 10/702,189

(22) Filed: Nov. 5, 2003

(65) Prior Publication Data

US 2005/0021062 A1    Jan. 27, 2005

(51) Int. Cl.
A61B 17/08    (2006.01)

(52) U.S. Cl. .................................................... 606/151

(58) Field of Classification Search ............... 606/138, 606/139, 142, 143, 151, 157, 158, 141; 24/456, 24/546

See application file for complete search history.

(56) References Cited

U.S. PATENT DOCUMENTS

| | | | |
|---|---|---|---|
| 3,797,076 A * | 3/1974 | Watkin ........................ | 24/562 |
| 4,274,415 A * | 6/1981 | Kanamoto et al. .......... | 606/142 |
| 4,325,377 A | 4/1982 | Boebel | |
| 4,556,060 A | 12/1985 | Perlin | |
| 4,658,822 A * | 4/1987 | Kees, Jr. ..................... | 606/158 |
| 4,775,426 A * | 10/1988 | Murley et al. ............... | 148/542 |
| 4,966,603 A | 10/1990 | Focelle et al. | |
| 4,976,722 A | 12/1990 | Failla | |
| 4,979,950 A | 12/1990 | Transue et al. | |
| 5,030,226 A | 7/1991 | Geen et al. | |
| 5,063,045 A * | 11/1991 | Namimatsu et al. .......... | 424/9.2 |
| 5,156,609 A | 10/1992 | Nakao et al. | |
| 5,303,226 A | 4/1994 | Okanoue et al. | |
| 5,312,426 A | 5/1994 | Segawa et al. | |
| 5,342,373 A | 8/1994 | Stefanchick et al. | |
| 5,474,567 A | 12/1995 | Stefanchick et al. | |
| 5,501,693 A | 3/1996 | Gravener | |
| 5,575,802 A | 11/1996 | McQuilkin et al. | |
| 5,593,414 A | 1/1997 | Shipp et al. | |

(Continued)

FOREIGN PATENT DOCUMENTS

DE    3238892    4/1984

(Continued)

OTHER PUBLICATIONS

International Search Report for PCT/US2004/023270.

(Continued)

*Primary Examiner*—Anhtuan T Nguyen
*Assistant Examiner*—Tuan V Nguyen
(74) *Attorney, Agent, or Firm*—Greenblum & Bernstein, P.L.C.

(57) ABSTRACT

An occlusion clip is disclosed that comprises an occlusion portion having an upper single element occlusion member having proximal and distal upper member ends and a lower single element occlusion member having proximal and distal lower member ends. The lower single element occlusion member and the upper single element occlusion member combine to define an occlusion member plane. The occlusion clip further comprises a spring portion having a torsion spring connecting the proximal upper member end to the proximal lower member end. The torsion spring has a spring height dimension in the occlusion member plane perpendicular to the upper and lower single occlusion members and is adapted to bias the upper and lower single element occlusion members toward a closed position wherein the upper single element occlusion member is in force contact with the lower single element occlusion member.

23 Claims, 22 Drawing Sheets

U.S. PATENT DOCUMENTS

| | | | |
|---|---|---|---|
| 5,601,573 | A | 2/1997 | Fogelberg et al. |
| 5,601,574 | A | 2/1997 | Stefanchik et al. |
| 5,634,932 | A * | 6/1997 | Schmidt ............... 606/157 |
| 5,681,330 | A | 10/1997 | Hughett et al. |
| 5,833,700 | A | 11/1998 | Fogelberg et al. |
| 5,858,018 | A | 1/1999 | Shipp et al. |
| 5,921,997 | A | 7/1999 | Fogelberg et al. |
| 5,993,465 | A | 11/1999 | Shipp et al. |
| RE36,720 | E | 5/2000 | Green et al. |
| 6,139,555 | A | 10/2000 | Hart et al. |
| 6,193,732 | B1 * | 2/2001 | Frantzen et al. ......... 606/151 |
| 6,241,740 | B1 * | 6/2001 | Davis et al. ............ 606/139 |
| 6,290,575 | B1 | 9/2001 | Shipp |
| 6,350,269 | B1 | 2/2002 | Shipp et al. |
| 6,352,541 | B1 | 3/2002 | Kienzle et al. |
| 6,464,710 | B1 | 10/2002 | Foster |
| 6,527,786 | B1 | 3/2003 | Davis et al. |
| 6,537,289 | B1 | 3/2003 | Kayan et al. |
| 6,599,298 | B1 | 7/2003 | Forster et al. |
| 6,607,540 | B1 | 8/2003 | Shipp |
| 6,652,539 | B2 | 11/2003 | Shipp et al. |
| 6,652,545 | B2 | 11/2003 | Shipp et al. |
| 6,679,894 | B2 | 1/2004 | Damarati |
| 6,824,547 | B2 | 11/2004 | Wilson, Jr. et al. |
| 6,849,079 | B1 | 2/2005 | Blake, III et al. |
| 6,869,435 | B2 | 3/2005 | Blake, III |
| 6,880,699 | B2 | 4/2005 | Gallagher |
| 6,911,033 | B2 | 6/2005 | de Guillebon et al. |
| 6,945,979 | B2 | 9/2005 | Kortenbach et al. |
| 2004/0097972 | A1 | 5/2004 | Shipp et al. |
| 2004/0106396 | A1 | 6/2004 | Segura et al. |
| 2004/0106936 | A1 | 6/2004 | Shipp et al. |
| 2005/0119677 | A1 | 6/2005 | Shipp |
| 2005/0149063 | A1 | 7/2005 | Young et al. |
| 2006/0129168 | A1 | 6/2006 | Shipp |

FOREIGN PATENT DOCUMENTS

| | | |
|---|---|---|
| WO | WO-99/52413 | 10/1999 |

OTHER PUBLICATIONS

Supplemental Search Report for EP2004757136.9.

* cited by examiner

OCCLUSION CLIP

CROSS-REFERENCE TO RELATED APPLICATIONS

U.S. application Ser. No. 10/626,966, filed Jul. 25, 2003, is incorporated herein by reference in its entirety.

BACKGROUND OF THE INVENTION

The present invention relates generally to mechanical devices used in surgical procedures to occlude a vessel or duct, and more particularly, to an instrument that can apply a pre-formed, spring-loaded clip used during surgery to clamp around a vessel or duct, such as cystic duct or cystic artery, and thereby obtain homeostasis or occlusion.

Those skilled in the art will appreciate that the use of clips for homeostasis or ligation during surgical procedures is well known. U.S. Pat. Nos. 4,976,722 and 4,979,950 for example, described prior art clips that are formed of titanium wire. Prior to use, these clips are "U-shaped" with a rectangular cross-section. Application of these prior art clips is normally effected by means of a crushing action produced by a clip applier, such as that disclosed in U.S. Pat. No. 5,030,226. Such crushing action permanently deforms the clips, making them difficult to remove or re-position. Another problem with crush clips is that vessels and tissue often shrink after occlusion owing to the onset of necrosis, for example. Because these type clips have no means for compensating for shrinking tissue, they lose their occlusion properties.

Numerous spring clips have been developed for occluding tissue. U.S. Pat. Nos. 4,966,603, 4,274,415, 5,833,700 and 6,350,269 disclose examples of spring clips. One problem with the clips described in the '603, '415, and '700 patents is that the occlusion force exerted by the clips approaches zero as the opposing occlusion members come into contact. Thus, for very thin tissue, the clips supply nearly zero occlusion force.

Other problems are presented by the clip of the '269 patent. For example the clip of the '269 patent is too wide for many intricate procedures and its configuration is difficult to manufacture. In addition, this clip is difficult to remove under laparoscopic conditions.

Some spring clips, such as those clip described in U.S. Pat. No. 4,556,060, are designed for placement on tissue in the surgical field by hand. Other clips, such as that described in U.S. Pat. No. 4,274,415, are applied using applicators that are suitable for use in open surgery but not for laparoscopic surgery. One applicator that is suitable for use in laparoscopic surgery is the applicator disclosed in the '269 patent. The clip and applicator combination of the '269 patent have several problems, however. For example, the clip has a narrow proximal end and the feed track in the clip holder is relatively wide. This causes the clip stack to kink, which causes excessive friction during clip feed. This can result in the clip pusher slipping over clips and clips jamming. Also, the jaws of the applicator are necessarily wide in order to accommodate the wide distal end of the clip. This does not allow adjacent clips to be placed in close proximity as is often required in delicate procedures. Another disadvantage of the '269 system is that surgeons are accustomed to viewing clips as they are being applied. Crush clips, for example, are fully visible before crushing. Viewing of the clip during application in '269 is limited to the view of a small portion of the clip through one of two small windows in the jaws. Yet another problem is that the applicator described in '269 patent uses a sacrificial clip to push the last usable clip onto the jaws for application. The sacrificial clip remains in the applicator, unusable, since there is no reliable means to push it out. Sometimes, the pusher clip is partially fed into the jaws, which causes the jaws to become attached to the tissue with no way to extricate the clip and free the jaws. Finally, resetting the applicator to the initial state so that the applicator is ready to place a second clip is often a problem.

What is needed is a simple-to-manufacture, easy-to-remove, narrow spring clip that maintains a substantial occlusion force to the occlusion members of the clip when they are at or near the closed position so that small vessels and ducts can be adequately occluded.

SUMMARY OF THE INVENTION

An exemplary embodiment of the present invention provides an occlusion clip comprising an occlusion portion having an upper single element occlusion member having proximal and distal upper member ends and a lower single element occlusion member having proximal and distal lower member ends. The lower single element occlusion member and the upper single element occlusion member combine to define an occlusion member plane. The occlusion clip further comprises a spring portion having a torsion spring connecting the proximal upper member end to the proximal lower member end. The torsion spring has a spring height dimension in the occlusion member plane perpendicular to the upper and lower single occlusion members and is adapted to bias the upper and lower single element occlusion members toward a closed position wherein the upper single element occlusion member is in force contact with the lower single element occlusion member. The occlusion clip may also comprise a clip guide portion having an upper clip guide attached to the distal end of the upper single occlusion member and a lower clip guide attached to the distal end of the lower single occlusion member. The upper clip guide includes a first planar member having a top upper guide surface and an engaging bottom upper guide surface. The first planar member is perpendicular to the occlusion member plane when the upper and lower single occlusion members are in engagement. The lower clip guide includes a second planar member having a bottom lower guide surface and an engaging top lower guide surface. The second planar member is parallel to the first planar member when the upper and lower single occlusion members are in engagement.

Other features and advantages of the present invention will be readily apparent to those skilled in the art upon a reading of the following disclosure when taken in conjunction with the accompanying drawings

DETAILED DESCRIPTION OF THE INVENTION

Figure 1:
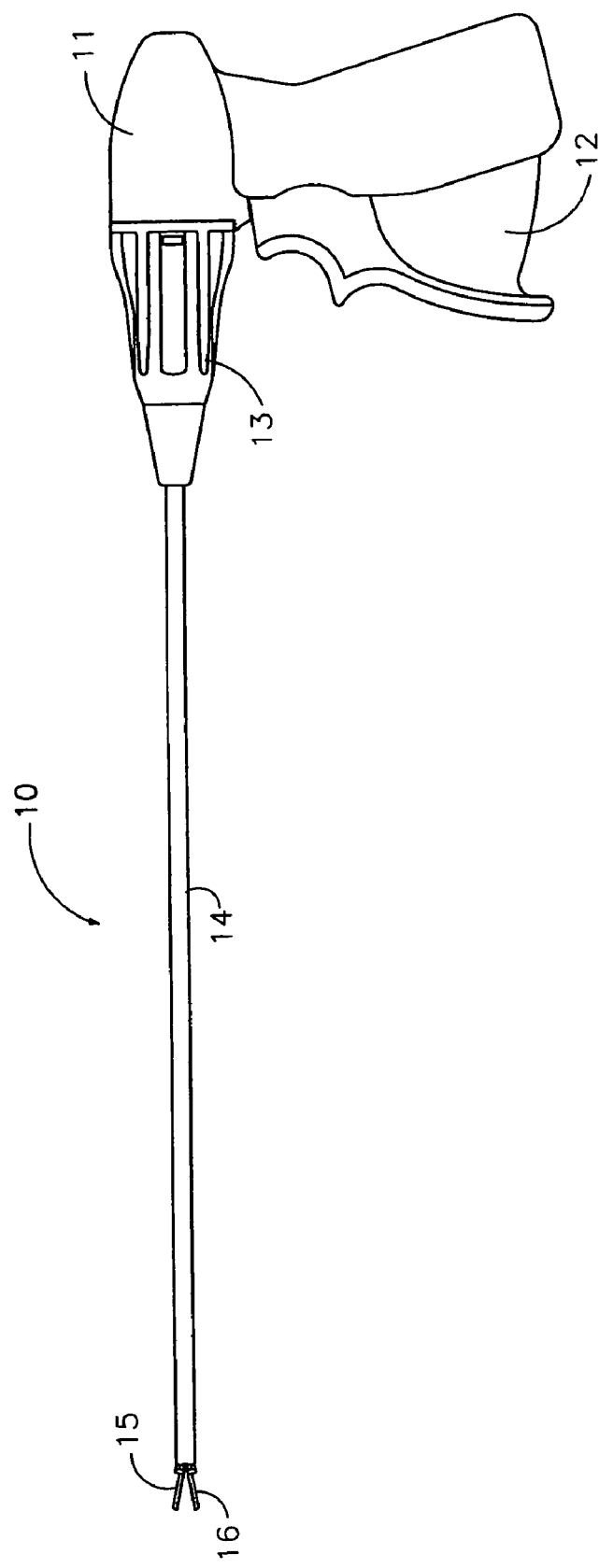
FIG. 1 is a side view of an applicator in an un-stroked state according to an embodiment of the invention.

The present invention provides a simple spring action surgical clip and an instrument to apply it. The clip may be made from a single piece of titanium alloy wire. It has single element occlusion members connected by a single torsion spring or connecting coil that biases the members together for occluding tissue after the clip has been opened for placement. The clip may be pre-formed so that in its equilibrium or near equilibrium state, it can be easily placed within the surgical field through a trocar cannula of 5 mm diameter or less. After the instrument containing one or more of the clips is inserted into the cannula in the vicinity of the tissue to be clamped, the clip is advanced distally, staying longitudinally aligned because of the narrow opening in the clip holder. As the clip enters the jaws of the applicator, the occlusion members of the clip are spread such that they pass axially over the jaws, thus increasing the tension in the connecting coil. With the tissue clamped between the jaws, the clip is further urged distally until the clip guides at the distal end of the occlusion members reach the release openings in the jaws, at which point the restoring force exerted by connecting coil forces the clip arms back toward the equilibrium position so that they can engage the tissue to be occluded. When the applicator jaws are opened, the tissue with the clip clamped thereon is detached from the instrument.

The clip width of the present invention is determined by the width of the wire used to form the clip. Other than the clip guides at the distal end of each occlusion member, which can be designed to be quite small, the clip width is equal to the wire diameter for clips formed from circular wire. For comparison, the clip described in the '269 patent is more than 5 wire diameters wide at the distal end. To control the placement of the clip of the '269 patent, it is required that the jaws be even wider, making the device unusable for small delicate applications. Compounding the size issue, except for small windows in each jaw, the large clip is hidden from the surgeon's view during placement. The clip and placement instrument of the present invention is usable in much smaller spaces and the placement instrument provides for much better visibility during the placement process.

The applicator of the current invention employs a simple, inexpensive clip follower that allows all the clips in the applicator to be used. It is designed such that it will not exit the clip holder and become stuck in the jaws. As a further advantage, the applicator of this invention minimizes the reset force, which results in a lower trigger pull force.

The invention will now be described in more detail. A surgical occlusion clip according to an embodiment of the invention includes two single element occlusion members joined by a bias structure, most simply a single torsion coil, or a portion of a single torsion coil, all lying in the same plane. Each occlusion member of the clip includes an enlarged clip guide section, the purpose of which is to control the clip throughout the placement process. The clip is integrally formed from a single length of wire with the clip guides formed on the wire by coiling or other similar processes. The clip can be manufactured using wire of rectangular, circular or other constant cross section shapes. In an illustrative embodiment, the wire may have a maximum thickness in a range from about 0.01 to about 0.05 inches (10 to 50 mils). In a particular embodiment, the wire has a circular cross section with a diameter in the range of 0.02 to 0.04 inches (20 to 40 mils) and is made from an implantable grade titanium alloy. The outside diameter or height of the torsion spring—and hence its inside dimension—increases as the occlusion members are separated. The clip is formed and can be heat-treated in such a way that it provides a clamping force of at least 0.20 pounds between the occlusion members when the clip is fully closed. Owing to the way in which the torsion spring is wound, the coil becomes slightly smaller as the occlusion members move toward the closed position. Conversely, the torsion spring grows slightly as the clip is opened.

In the applicator of the present invention, the clips described above are held, in a partially open state in contact with each other, end-to-end, in a clip holder, a component of the applicator. The clip holder comprises two parallel rails separated by a width nominally larger than the clip width. One clip guide rests on the top of the rails with the other clip guide on the bottom such that the clip is held in a partially open state by the thickness of the material of the clip holder rails. The opening between the rails is only slightly larger than the clip width but is not as wide as the width across the clip guides so that the clip can be moved down the length of the clip holder with little side-to-side movement, always remaining in the partially opened state. An inverted U-shaped reciprocating rod equipped with clip guide engagement fingers moves the clips distally toward the jaws with minimal friction. The clip holder is anchored relative to the jaw actuator in a rotator which is attached to a pistol grip handle.

A clip follower engages the last clip and, when the clip holder is fully loaded, is engaged by the proximal-most clip push fingers. The clip follower allows the ejection of all clips loaded in the clip holder such that there is no need to leave a unused clip in the applicator, which may be a disposable device.

Two articulated jaws are attached to the distal end of the clip holder. The jaws have two rectangular sections the openings of which butt pivotally together against the rectangular section of the clip holder such that as the clip is urged distally. One clip guide enters the interior of the rectangular section of one jaw and the other clip guide enters the interior of the rectangular section of the other jaw thus retaining control of the clip against side-to-side movement or closure. Depending upon the thickness of the jaw material and the tissue thickness, the clip may be further opened at the transition between the clip holder and the jaws. A release opening is formed at the distal end of each jaw such that the clip guides of the clip are no longer constrained by the jaws upon the clip reaching the distal end, thus the clip closes about the tissue and compresses the tissue because of the tension stored in the coil of the clip. The jaws are formed in an open frame arrangement so that the clip is totally visible throughout the placement process thus eliminating the viewing windows of the prior art. Additionally, the jaw width is only slightly wider than the clip, making the clip very useable in small narrow spaces.

An actuator is operably connected to the jaws. The actuation of which moves the jaws between a first position in which the jaws are open and a second position in which the jaws are closed.

Upon release of the activating trigger a reset spring returns the jaw actuator and the clip pusher to their initial positions, the clip stack being then one clip shorter. The clip pusher is formed in an inverted U-shape with clip engagement fingers on either side so that the clip pusher need only clear the clip guides while resetting, not the larger torsion spring as in the prior art. This significantly lessens the return force requirement of the reset spring and lowers the space requirement for containing the mechanisms.

Figure 2:
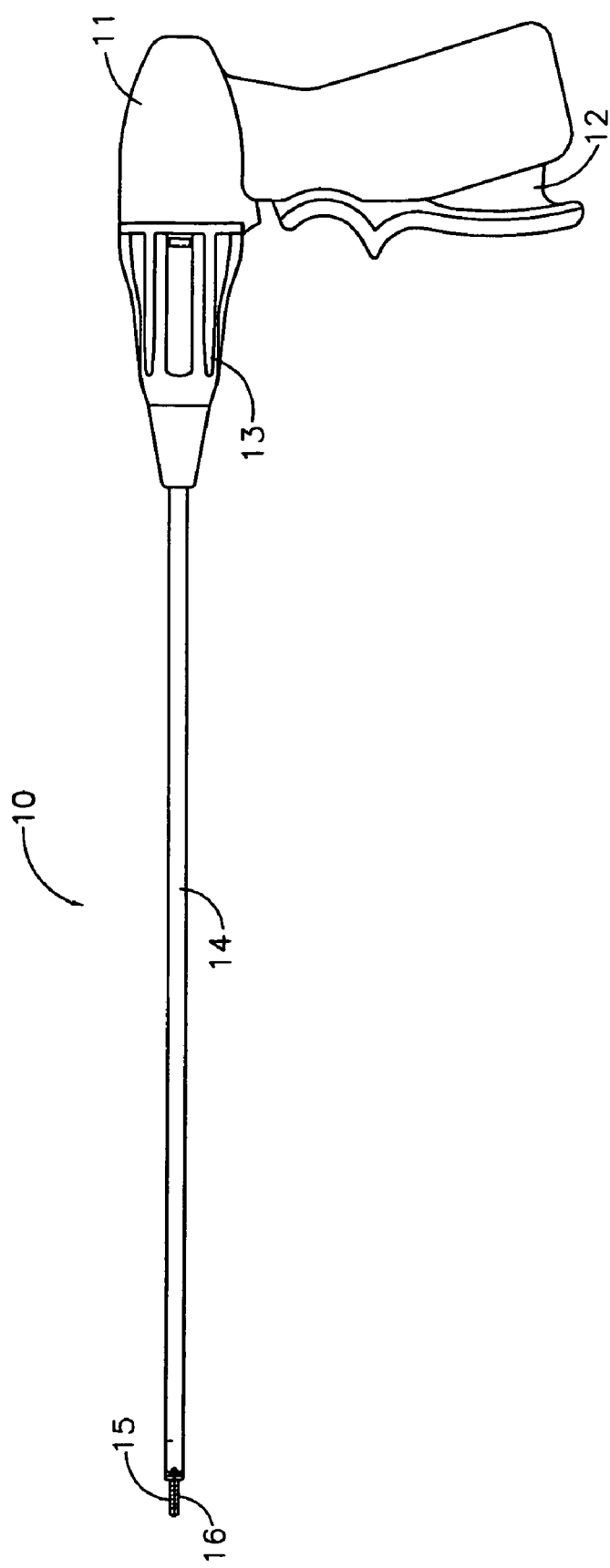
FIG. 2 is a side view of an applicator in a stroked state according to an embodiment of the invention.

Referring now to the drawings, and particularly to FIGS. 1 and 2, an occlusion clip applicator is shown and generally designated by the numeral 10. Applicator 10 includes a body or handle subassembly 11 and a rotator subassembly 13.

Figure 9:
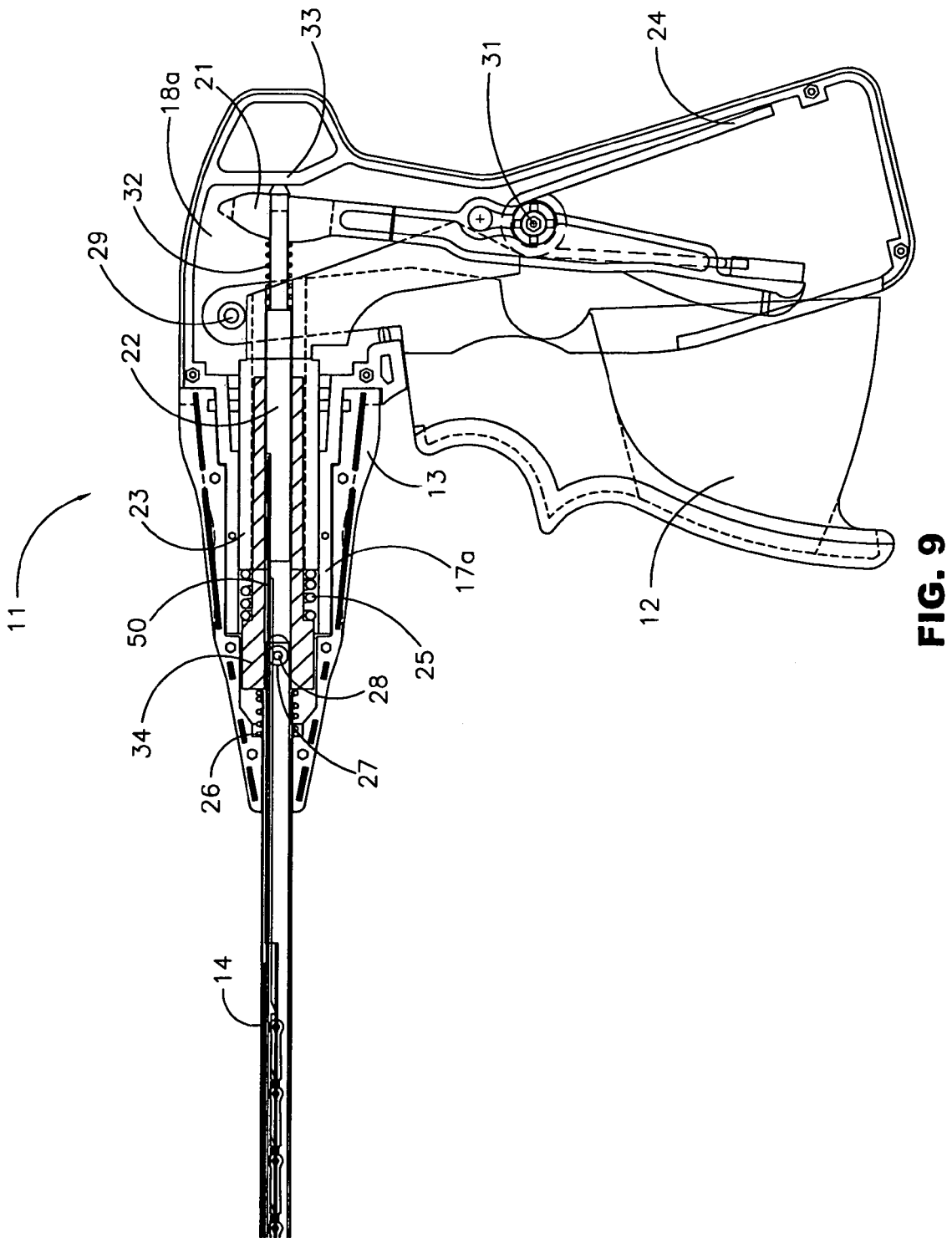
FIG. 9 is a cross section of the handle of an applicator according to an embodiment of the invention.

Referring to FIG. 9, the handle subassembly 11 comprises two handle halves 18a, one of which has been removed to allow the internal components of the handle subassembly 11 to be viewed. A distally extending handle projection 17a is integrally formed with each of the handle halves 18a. When the handle halves 18a are joined, these projections 17a form a cylinder extending distally from the joined halves 18a. The two handle halves 18a fit together in a welded or press-fit fashion and house a jaw actuator and a clip actuator. The jaw actuator comprises first pusher 23, first pusher spring 25 and second pusher 34. The clip actuator comprises clip cylinder 22 and cylinder spring 32. A lever 21 connects to both the clip actuator and the jaw actuator to trigger 12 and rotates about axis 31 when urged to rotate by movement of the trigger 12. The trigger 12 rotates about a pivot 29 under the pull force of the user's hand. A torsion spring 24 is attached to lever 21, abuts handle half 18a, and provides a reset force for both actuators.

Figure 14:
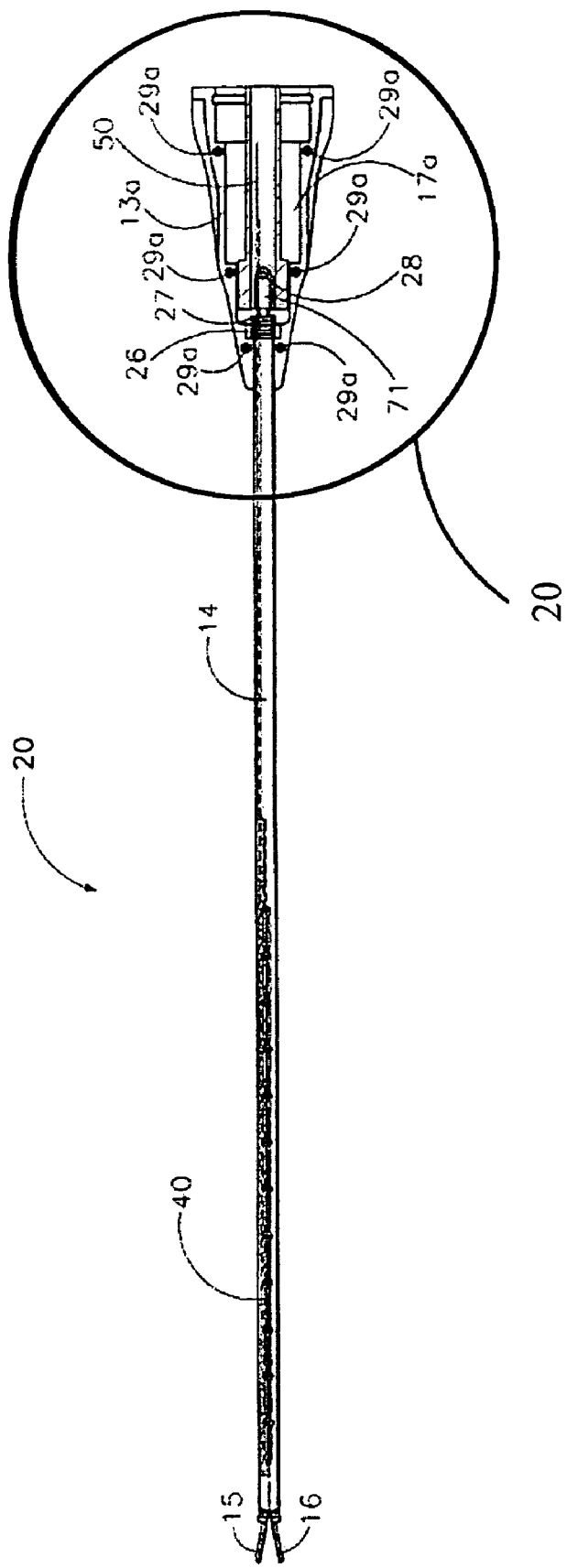
FIG. 14 is a cross section of the jaw actuator tube and the rotator of an applicator according to an embodiment of the invention.
Figure 20:
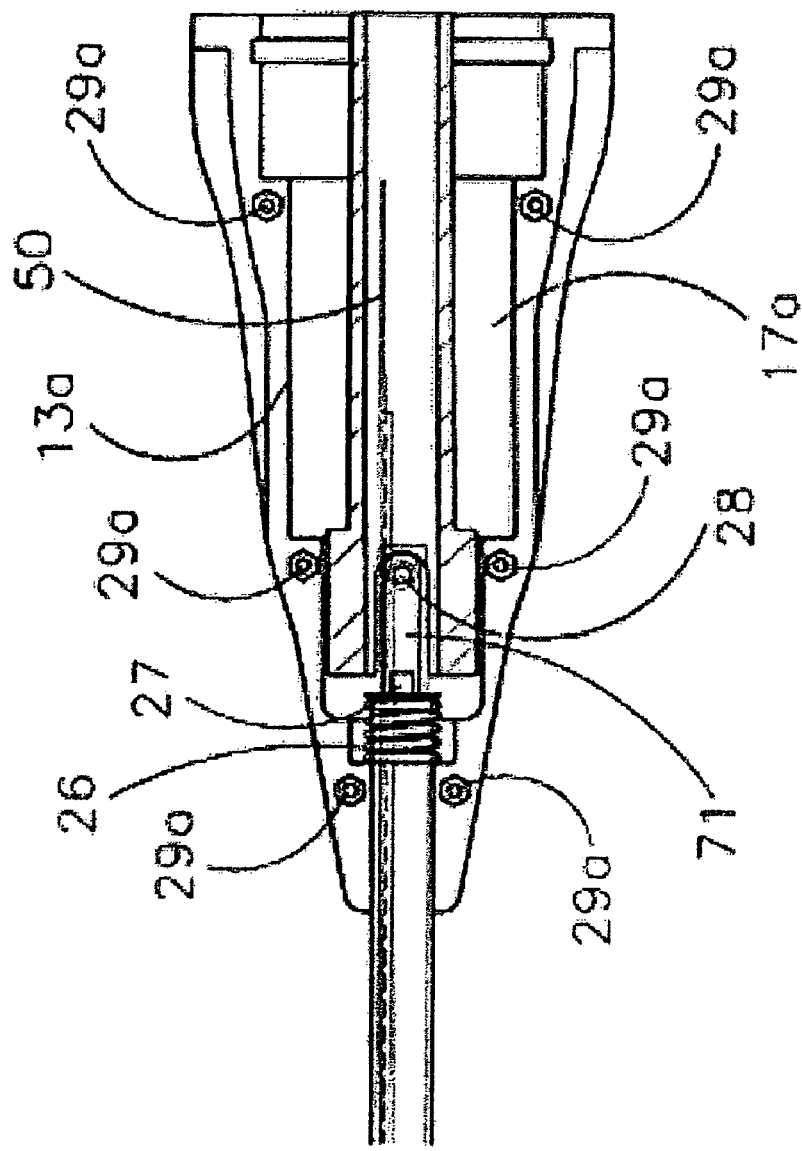
FIG. 20 is a section view of a rotator portion of an applicator according to an embodiment of the invention.

FIGS. 14 and 20 depict the rotator subassembly 20, comprising two rotator halves 13a (one of which has been removed to allow the interior components of the rotator subassembly to be viewed), a clip holder 71, a jaw actuator tube 14, a jaw actuator tube spring 26, a clip push rod 50 and jaws 15 and 16. A plurality of clips 40 may be positioned within the clip holder 71 as will be discussed in more detail hereafter. The rotator half 13a contains a clip holder anchor pin 28 and a jaw push tube stop 27. The two rotator halves 13a may be held together by friction from alignment pins 29a in one of the rotator halves 13a and mating sockets (not shown) in the other rotator half or by welding or bonding the two halves 13a together.

The proximal end of the joined rotator halves 13a is received over the cylindrical handle extensions 17a to join the rotator subassembly 20 to the handle subassembly 11. The subassemblies 11, 20 may be locked together by interlocking tabs. The rotator subassembly 20 is configured so that it can be rotated about its longitudinal axis relative to the handle subassembly 11.

Now turning to FIGS. 3-8, depicting various views of a clip 40 according to an embodiment of the present invention. The clip 40 is described below relative to the three axes L, P1, and P2 shown in FIG. 7. Longitudinal axis L defines the longest portion of clip 40. Vertical axis P1 is perpendicular to axis L and together with L defines a vertical plane L-P1 that contains torsion spring coil 41. Lateral axis P2 is perpendicular to the vertical plane L-P1. Lateral axis P2 and longitudinal axis L together define a horizontal plane L-P2. It will be understood by those of ordinary skill in the art that the terms lateral, vertical and longitudinal are intended to describe a space relative to the clip 40 and not to indicate a fixed position relative to the space in which the clip 40 is to be positioned.

Figure 3:
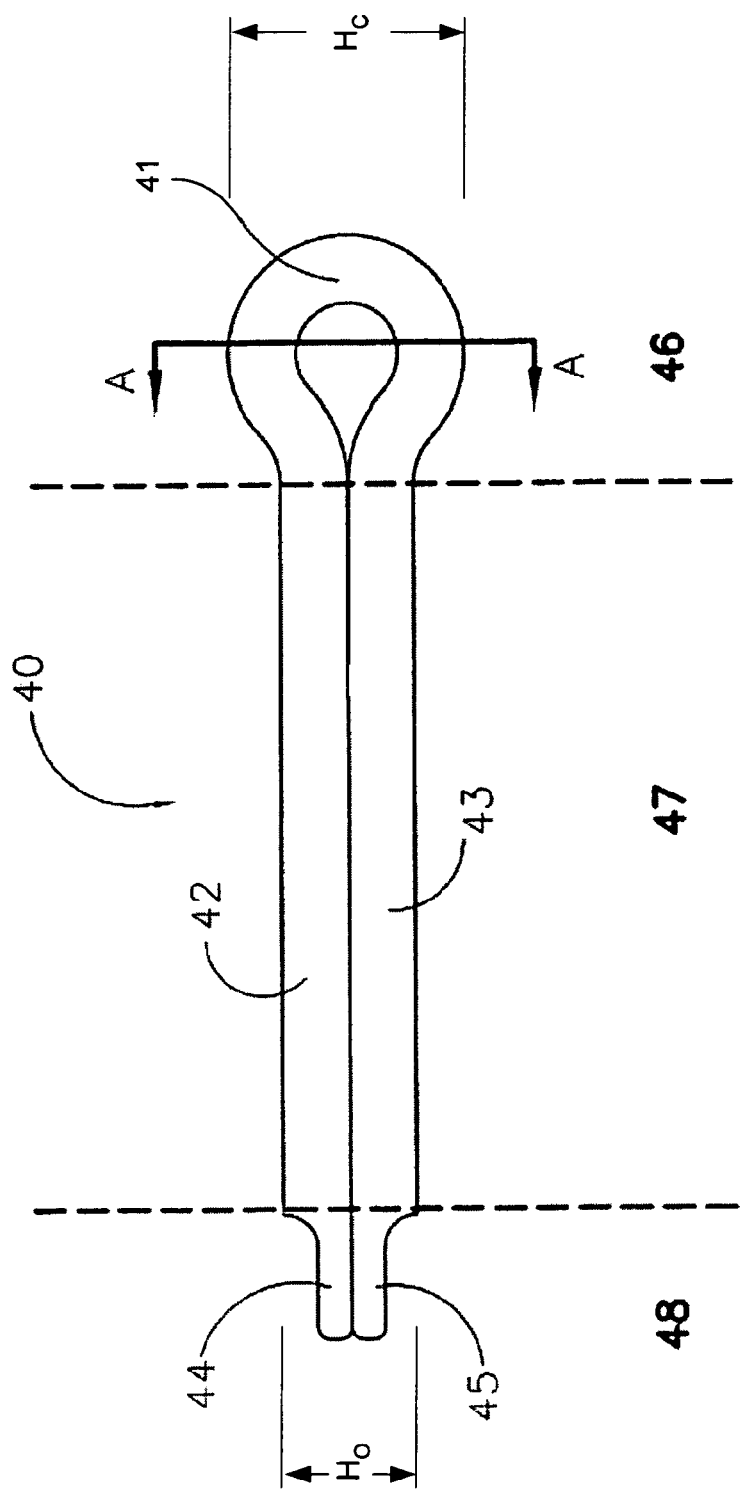
FIG. 3 is a side view of an occlusion clip according to an embodiment of the invention.
Figure 4:
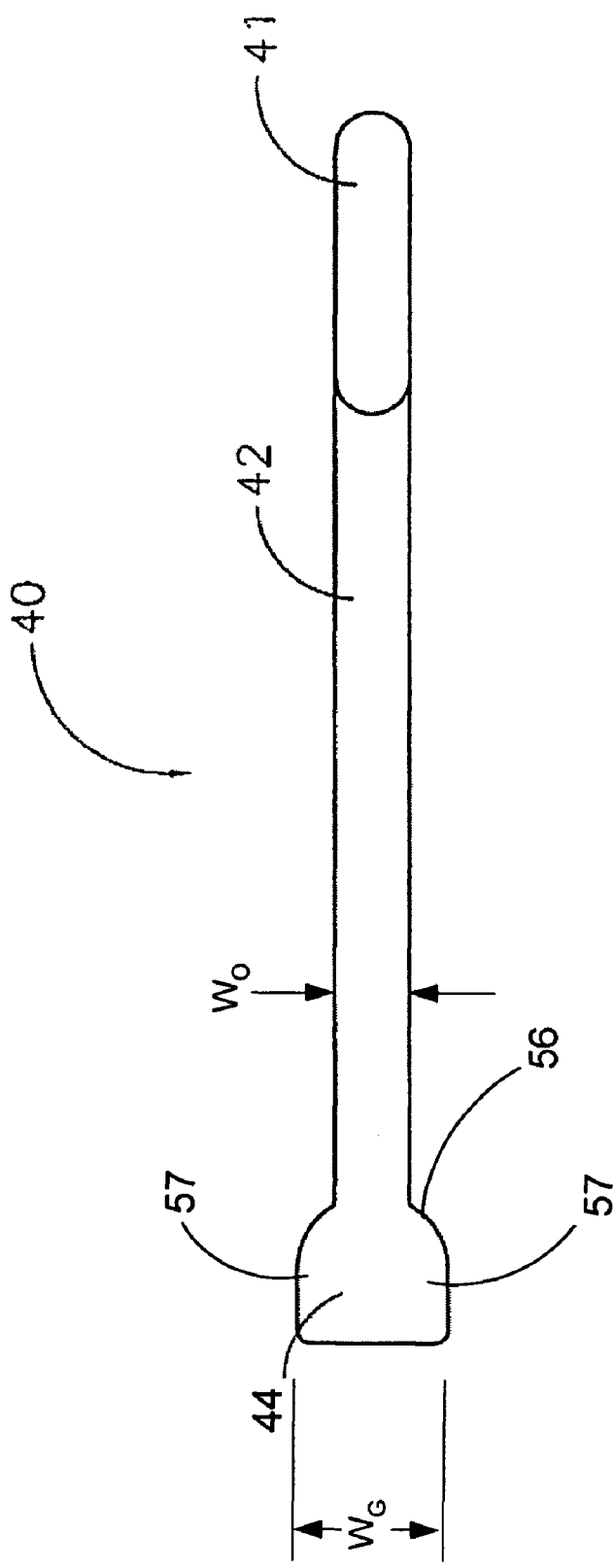
FIG. 4 is a plan view of an occlusion clip according to an embodiment of the invention.

FIG. 3 shows a clip 40 divided into a torsion spring section 46, an occlusion member section 47 and a clip guide section 48. In this embodiment, the torsion spring section 46 comprises a single wire loop 41 connected to the occlusion member section 47. One end of the torsion coil 41 is connected to a single element upper occlusion member 42, and the opposite end of the torsion coil 41 is connected to a lower single element occlusion member 43. The upper occlusion member 42, the torsion spring 41, and the lower single element occlusion member 43 are all centered within the vertical plane L-P1. When the clip 40 is in the closed configuration shown in FIG. 3, the height $H_O$ of the occlusion portion 47 in the vertical plane L-P1 is no more than two times the diameter of the wire used to form the clip 40. In the closed configuration, the single element occlusion members 42, 43 are substantially parallel. FIG. 4 depicts a plan view of clip 40. The width $W_O$ of the occlusion section 47 in the plane L-P2 is equal to the diameter of the wire used to form the clip 40.

Figure 6:
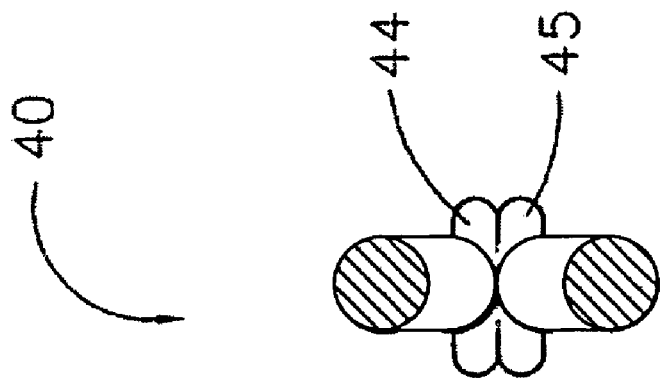
FIG. 6 is a cross sectional view of an occlusion clip according to an embodiment of the invention.
Figure 5:
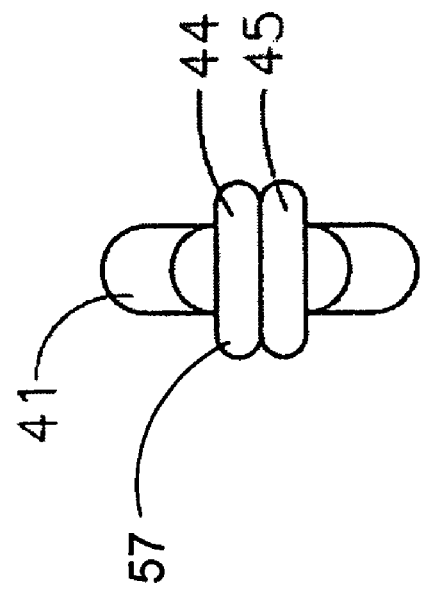
FIG. 5 is an end view of an occlusion clip according to an embodiment of the invention.
Figure 8:
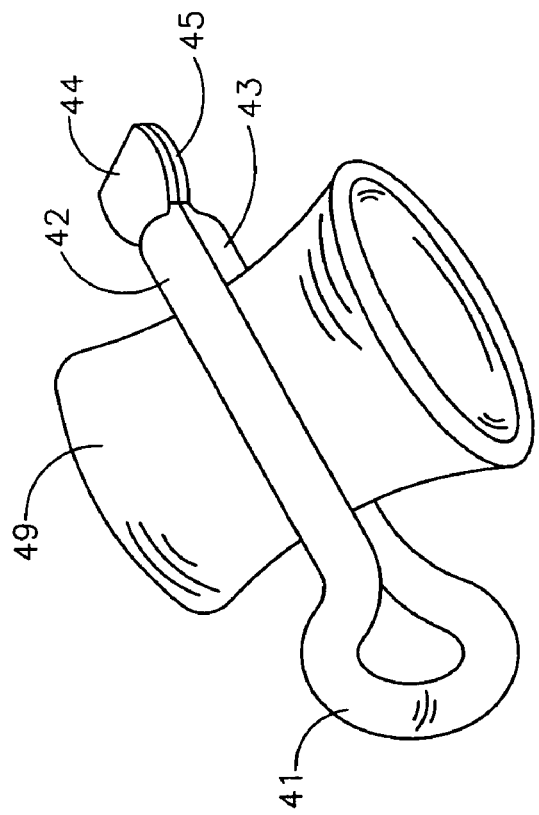
FIG. 8 is an isometric view of an occlusion clip according to an embodiment of the invention wherein the clip is applied to a vessel.
Figure 7:
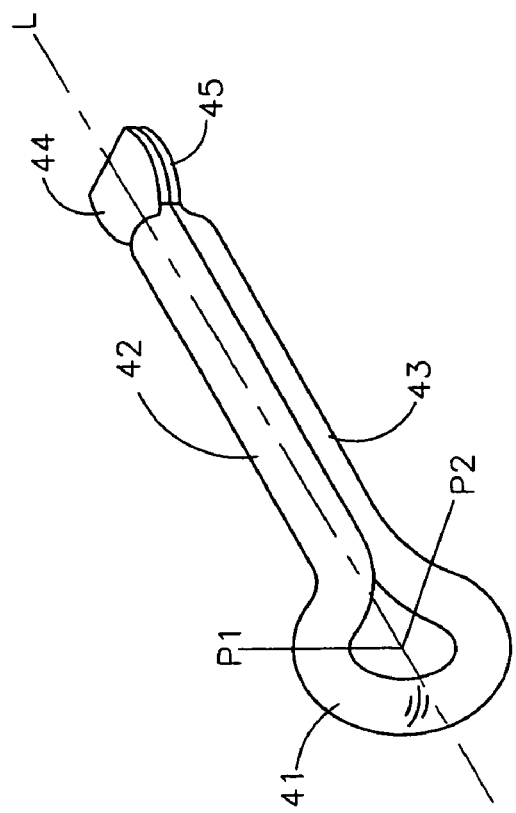
FIG. 7 is an isometric view of an occlusion clip according to an embodiment of the invention.

The clip guide section 48 comprises the clip guides 44, 45 which are connected to the upper and lower occlusion members 42, 43 respectively. The clip guides 44, 45 may be formed as planar members having an engagement surface that is approximately coplanar with the inner engaging surfaces of the occlusion members 42, 43. The clip guides may have a proximal edge 56 that is configured for engagement by the fingers 51a, 51b of a clip push rod 50 of the applicator 10 as will be discussed hereafter. As will also be discussed, the width $W_G$ of the clip guides 44, 45 is established so that the lateral edge portions 57 of the clip guides as seen in FIG. 5 and proximal edge 56 as shown in FIG. 6 can engage the rails 72a, 72b of the clip holder 71. FIG. 5 shows a distal end view of the clip 40 and FIG. 6 depicts a section view of the clip 40 through the torsion coil 41. FIG. 8 shows the clip 40 with the occlusion members 42, 43 occluding a vessel 49.

Figure 10:
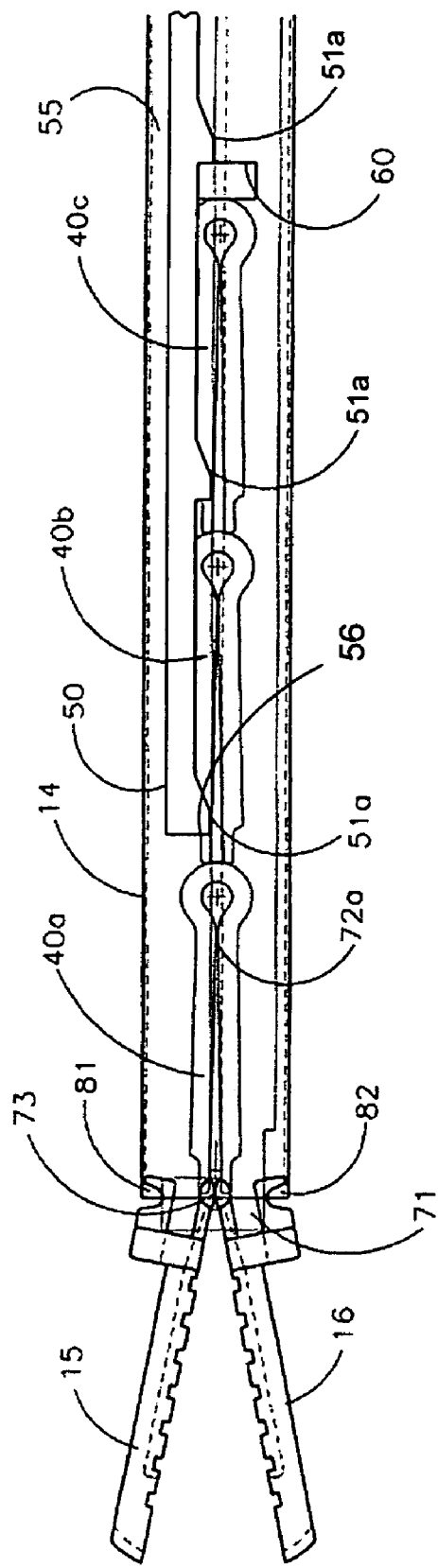
FIG. 10 is a longitudinal cross section of the distal section of an applicator according to an embodiment of the invention.
Figure 11:
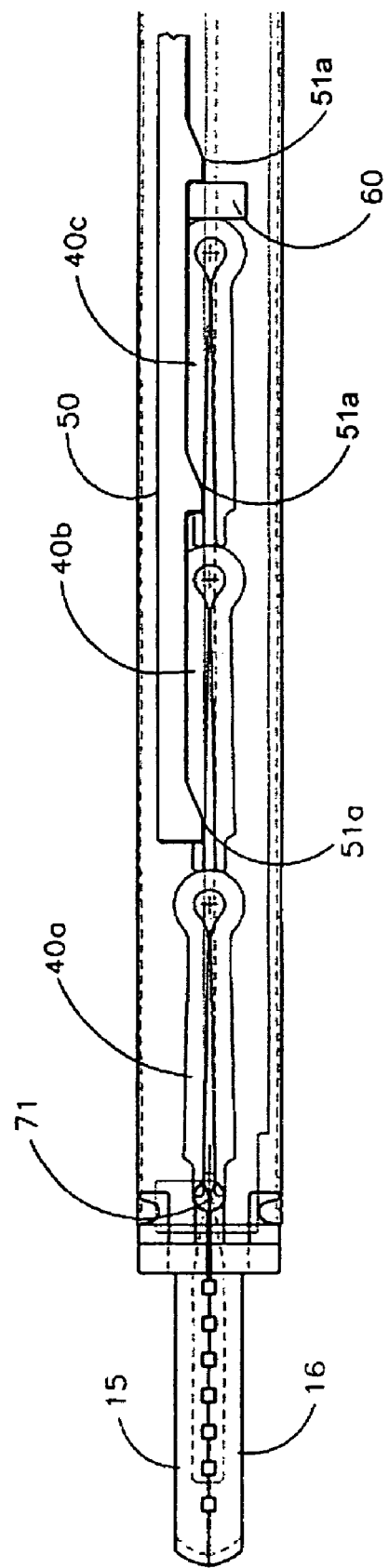
FIG. 11 is a longitudinal cross section of the distal section of an applicator according to an embodiment of the invention wherein the jaws are in a closed position.
Figure 12:
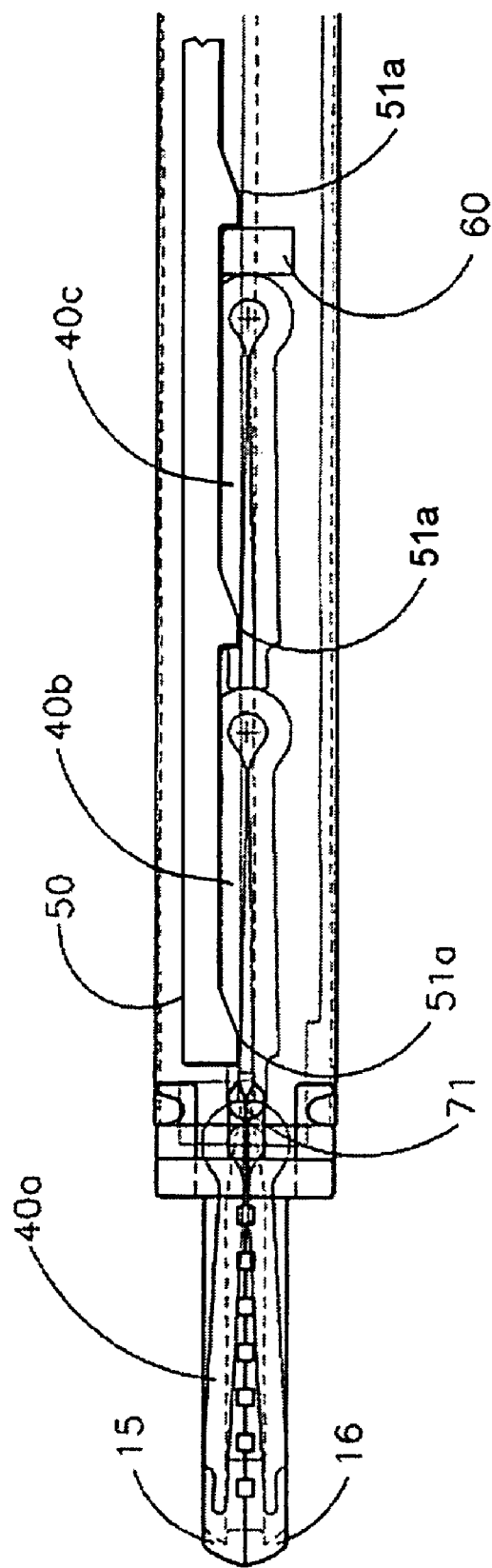
FIG. 12 is a longitudinal cross section of the distal section of an applicator according to an embodiment of the invention when the applicator is in a fully stroked position.

FIGS. 10, 11, and 12 are longitudinal cross sections of the distal end of the applicator 10. FIG. 10 depicts the applicator 10 in the home, or ready-to-fire, position. In this position, clips 40a, 40b, and 40c are in proximal-to-distal contact with each other and the proximal-most clip 40a is positioned adjacent the entrance to the jaws 15, 16.

Figure 13:
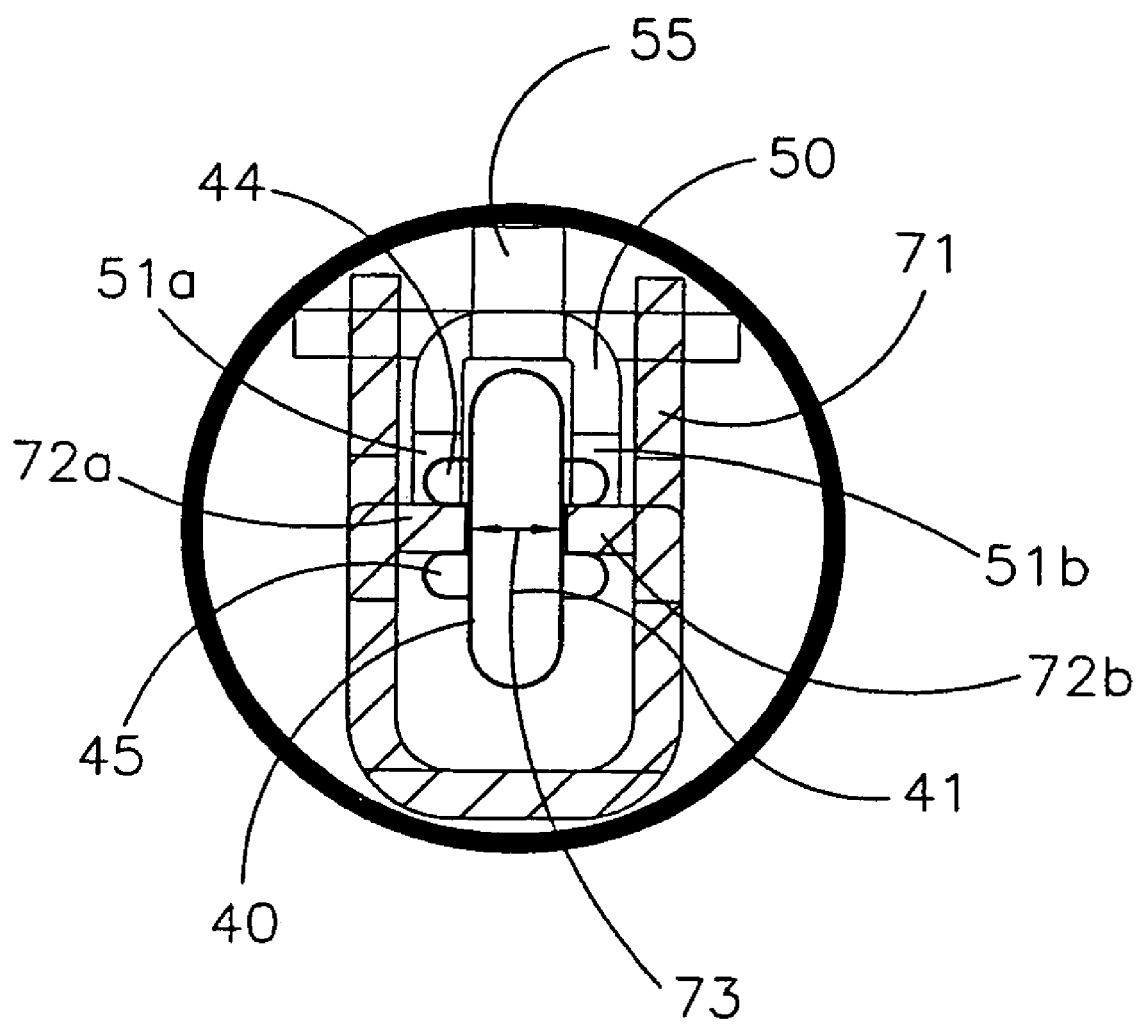
FIG. 13 is a cross section of the jaw actuator tube and the clip holder of an applicator according to an embodiment of the invention.

FIG. 13 shows a perpendicular cross section taken across jaw actuator tube 14. The clip holder 71 has a U-shaped cross-section with opposing first and second rails 72a, 72b extending inward into the center of the U. Clips 40 are positioned in the clip holder 71 so as to be held slightly open by the rails 72a, 72b. The rails 72a, 72b are engaged only by the lateral edge portion 57 of the clip guides 44, 45 of the clips 40. The slot 73 formed between the rails 72a, 72b is only nominally larger than the width $W_O$ of the occlusion clip section 47 and the torsion spring 46 so that the clips 40 are guided straight along their axis L with little side-to-side movement. To minimize the side-to-side movement of the clips 40, the slot 73 may have a width that is less than about 0.001 inches greater than the occlusion section width $W_O$ of the clip 40. Thus, for clips formed from 0.030-inch wire, the slot 73 may have a width in a range of about 0.0315 to about 0.0305 inches.

The clip push rod 50 comprises fingers 51a, 51b attached to an elongate shaft 59. The fingers engage the upper clip guide 44, and restoring spring 55, which contacts the inside surface of the jaw push tube 14 and biases the fingers 51a, 51b into engagement with the upper clip guide 44. The shaft 59 of the clip push rod 50 is attached at its proximal end to the clip cylinder 22. The clip push rod 50 is configured so that when the clip push rod is moved proximally, the fingers 51a, 51b are dragged over the clips 40 remaining in the clip holder 71. As they pass over the clips 40, the fingers 51a, 51b and the shaft 59 are deflected upwards to allow the fingers 51a, 51b to clear the clips 40. A compressible spacer (not shown) may be positioned above the shaft 59 of the clip push rod 50 to keep the fingers 51a, 51b in engagement with the clips 40.

The clip holder 71 is attached to upper and lower jaws 15, 16 at a jaw pivot 73. The jaw actuator tube 14 is attached to the jaws 15, 16 at attachment points 81, 82. The clip push rod 50 engages the upper clip guide 44 of each clip behind the proximal-most clip 40a and a clip follower 60 via fingers 51a, 51b. Although only three clips 40 are shown in FIGS. 10, 11, and 12, it will be understood that the applicator may be sized to accept any number of clips 40.

Figure 19:
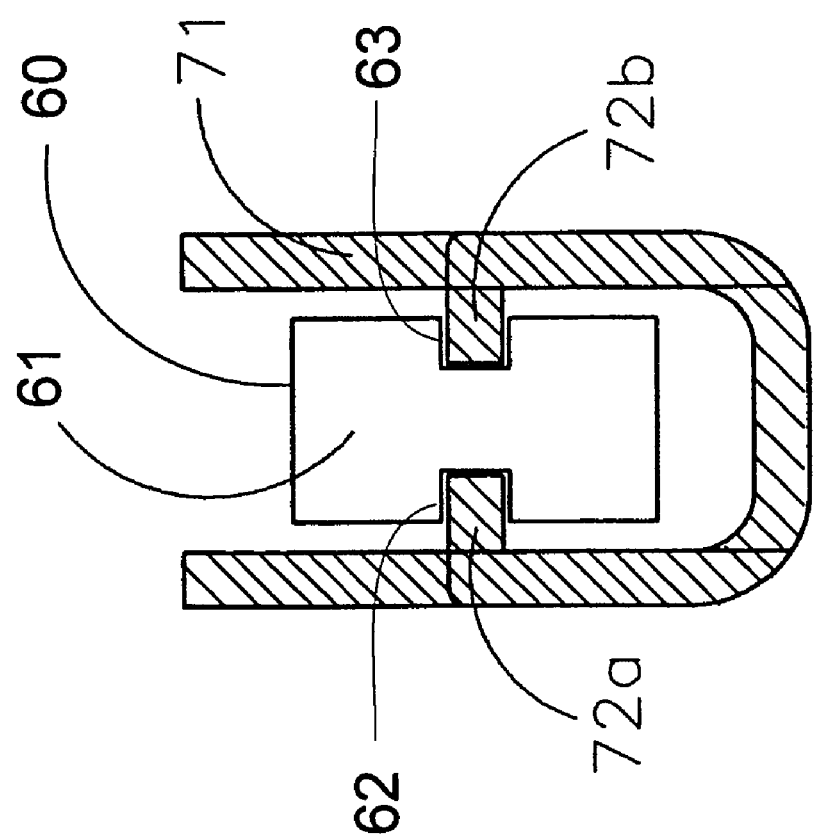
FIG. 19 is a cross-section of the clip holder and follower of an applicator according to an embodiment of the invention.

FIG. 19 is a cross-section of the clip holder 71 showing the follower 60. The follower 60 may be a solid or hollow body or, as will be discussed below, may be an elongate member bent to a desired shape. The follower 60 is configured with rail slots 62, 63 so that the follower 60 may be slidably mounted to the clip holder rails 72a, 72b. The follower 60 has a clip engaging surface 61 that engages the distal end of the distal-most clip 40c. The follower 60 may be attached to or may be configured to be engaged by the clip push rod 50, FIG. 11 shows the proximal end of the applicator 10 in an intermediate configuration wherein the trigger 12 has been pulled proximally causing the first pusher 23 and second pusher 34 to move in the proximal direction. This causes the jaw actuator tube 14 to compress the jaw actuator tube spring 26 (first pusher spring 25 is less compressed because of its higher spring constant) and move proximally, thereby forcing causing the jaws 15, 16 to rotate about the jaw pivot 73 to a closed position.

FIG. 12 depicts the applicator 10 in a configuration where the trigger 12 is reaching its fully stroked position. In this configuration, the proximal-most clip 40a is pushed over the jaws 15, 16 by the second clip 40b, which has been urged proximally by the clip push rod 50 and by the distal-most clip 40c, which has in turn been urged proximally by the clip push rod 50 and by the follower 60.

Figure 15:
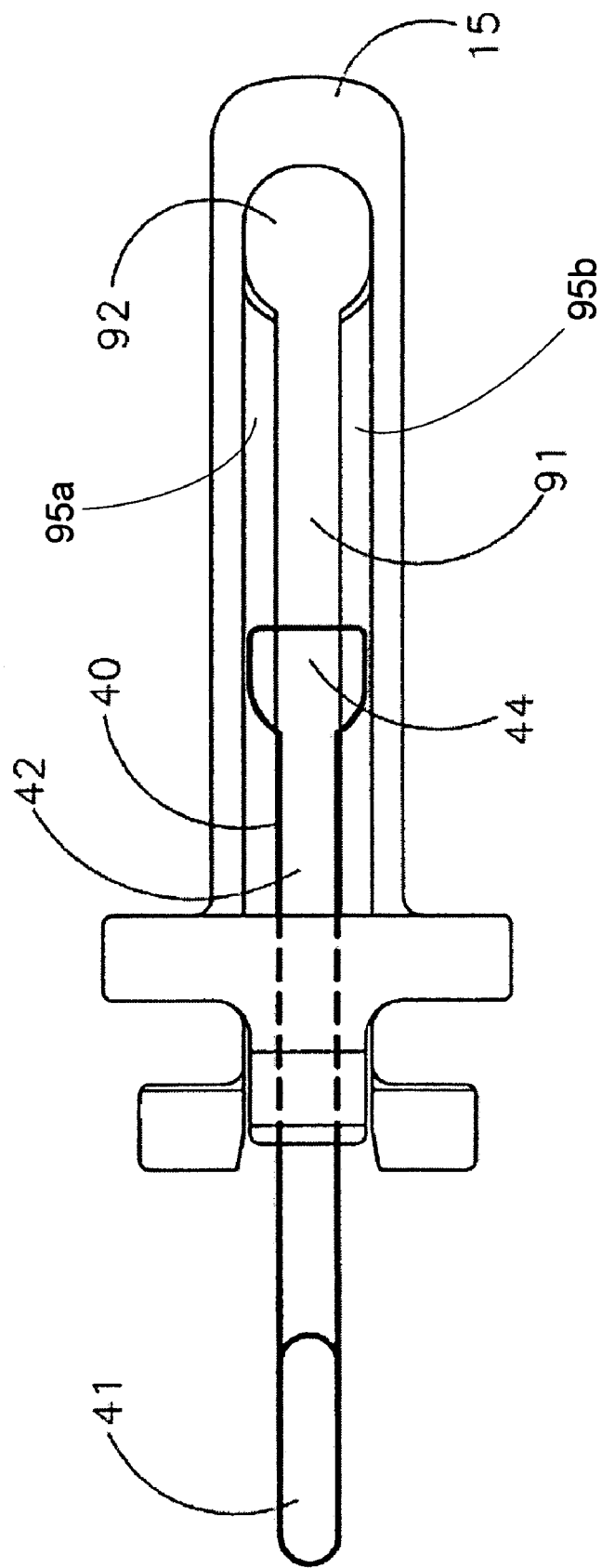
FIG. 15 is a plan view of the jaw of an applicator according to an embodiment of the invention with a partially stroked clip.
Figure 16:
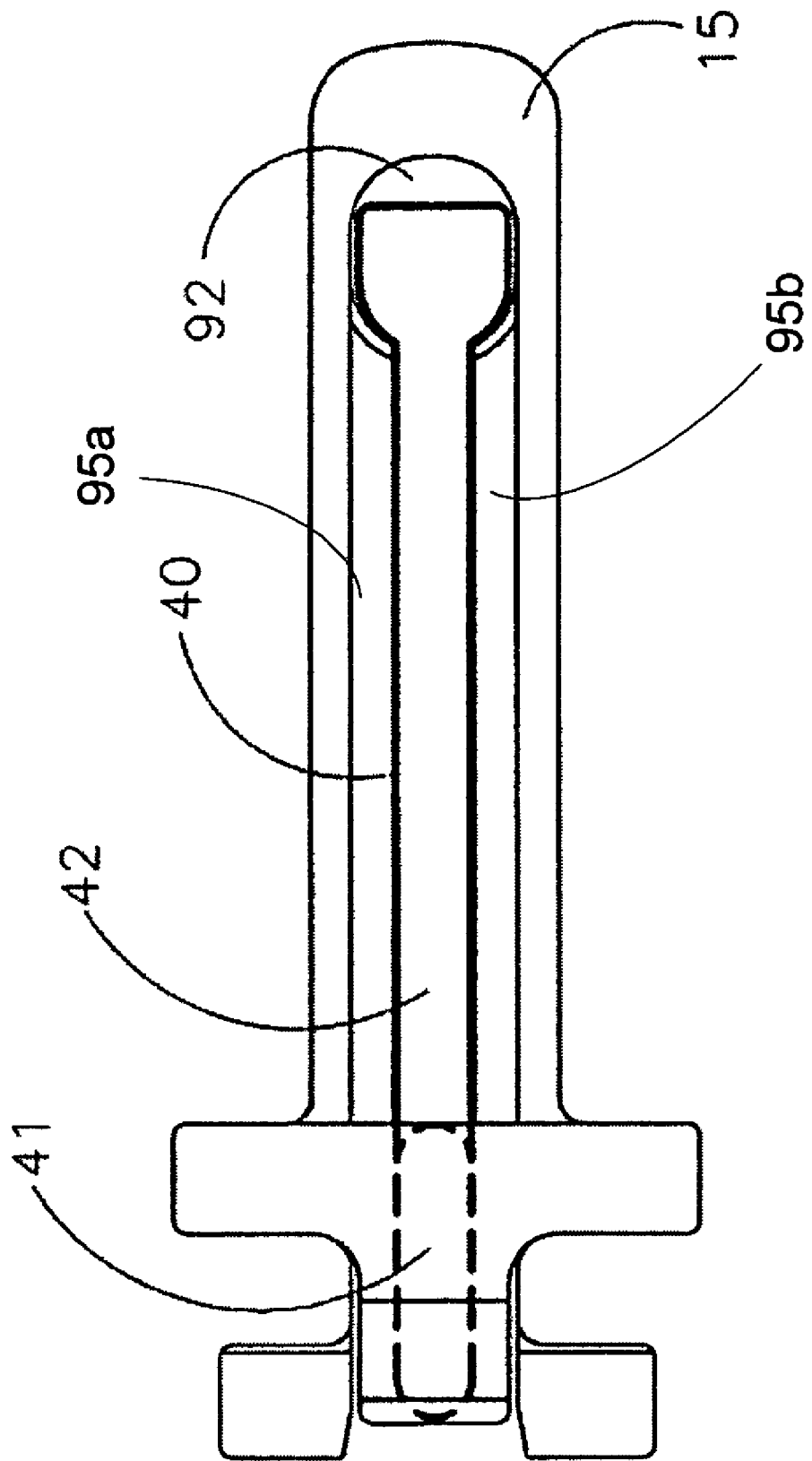
FIG. 16 is a plan view of the jaw of an applicator according to an embodiment of the invention with a fully stroked clip.

FIGS. 15 and 16 are plan views of the upper jaw 15 and a clip 40. It will be understood that the lower jaw 16 is simply a mirror image of and has identical features to the upper jaw 15. The jaw 15 has a jaw groove 91 flanked by entrance ramps leading to two jaw rails 95a, 95b. The jaw groove 91 terminates at its proximal end in a cut-out 92 sized to allow the clip guides 44, 45 to be passable therethrough. As was the slot 73 formed between the rails 72a, 72b of the clip holder 71, the jaw groove 91 is sized to be nominally larger than the width $W_O$ of the occlusion members 42, 43 and torsion spring coil 41 of clip 40. This allows the clip 40 to be moved proximally through the jaw groove 91 with little side-to-side motion. To minimize the side-to-side movement of the clips 40, the jaw groove 91 may have a width that is less than about 0.001 inch greater than the occlusion section width $W_O$ of the clip 40. Thus, for clips formed from 0.030-wire, the jaw groove 91 may have a width in a range of about 0.0305 to 0.0315 inches As the clip 40 is moved onto and along the jaws 15, 16, the lateral edge portions 57 of the clip guides 44, 45 engage opposite sides of the entrance ramps and jaw rails 95a, 95b, which keeps the clip 40 in an open state until the clip moves further distally as depicted in FIG. 16. When the clip guides 44, 45 reach the fall through cut out 92, they are released from the jaw rails 95a, 95b. The biasing force exerted by the torsion spring coil 41 causes the occlusion members 42, 43 to move toward a closed position. Any tissue 49 positioned between the occlusion members 42, 43 is engaged and occluded by the occlusion members as shown in FIG. 8. Because it is passed over the outside surface of the jaws 15, 16, the clip 40 is clearly visible throughout the transition over the jaws 15, 16 to the detached occluding condition.

Figure 23:
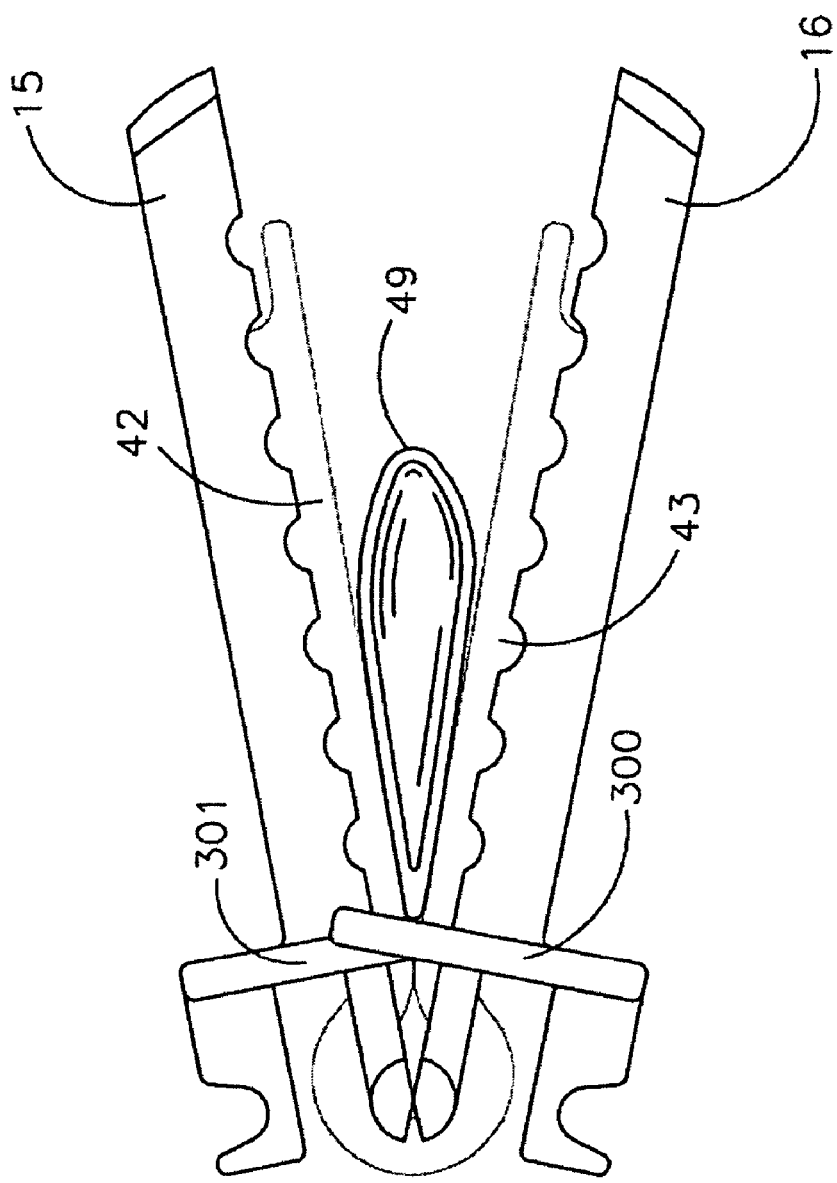
FIG. 23 is a side view of the jaws of an applicator according to an embodiment of the invention.
Figure 24:
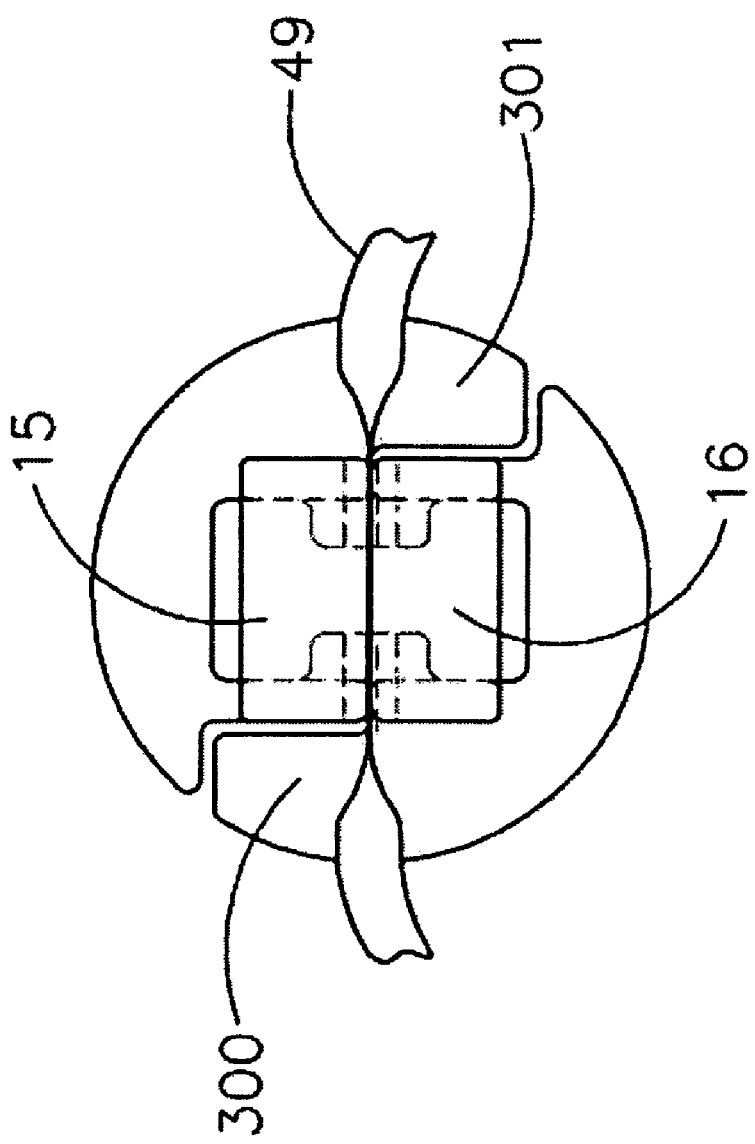
FIG. 24 is an end view of the jaws shown in FIG. 23.

FIGS. 23 and 24 illustrate an embodiment of the invention in which the jaws 15, 16 of the applicator includes tissue stops 300 and 301. The tissue stops 300, 301 are configured so that when a vessel 49 to be occluded is placed between the jaws 15, 16, the tissue stops 300, 301 abut the vessel 49 and position it so that the vessel is properly positioned within jaws 15, 16. This assures that the occlusion members 42, 43 of the clip 40 properly compress the vessel 49 and that the eyelet formed by the coil 41 of the clip is proximal to vessel 49. This assures that the vessel 49 is fully occluded.

Figure 17:
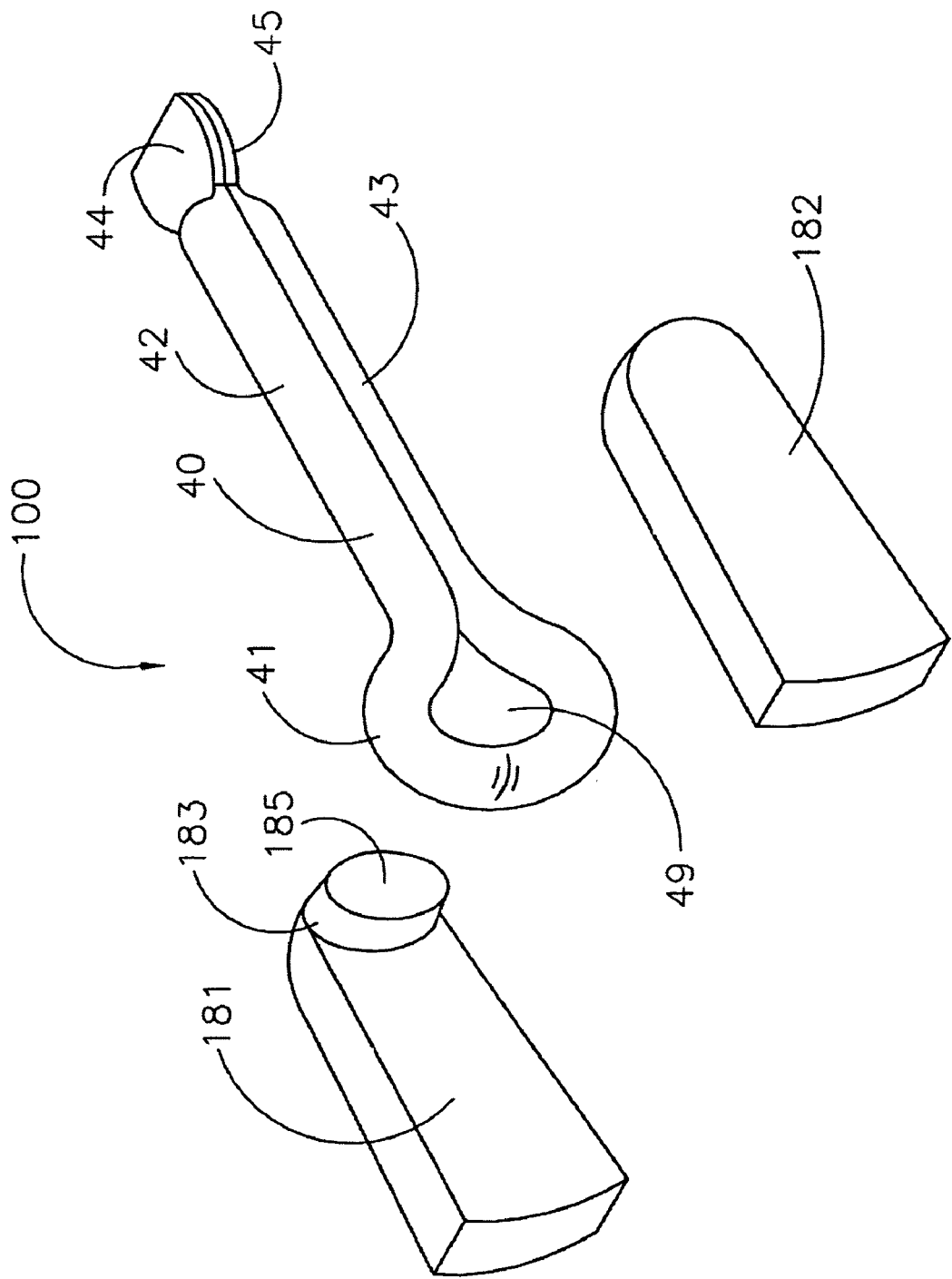
FIG. 17 depicts a clip remover and an occlusion clip according to an embodiment of the invention wherein the clip remover is not engaged.
Figure 18:
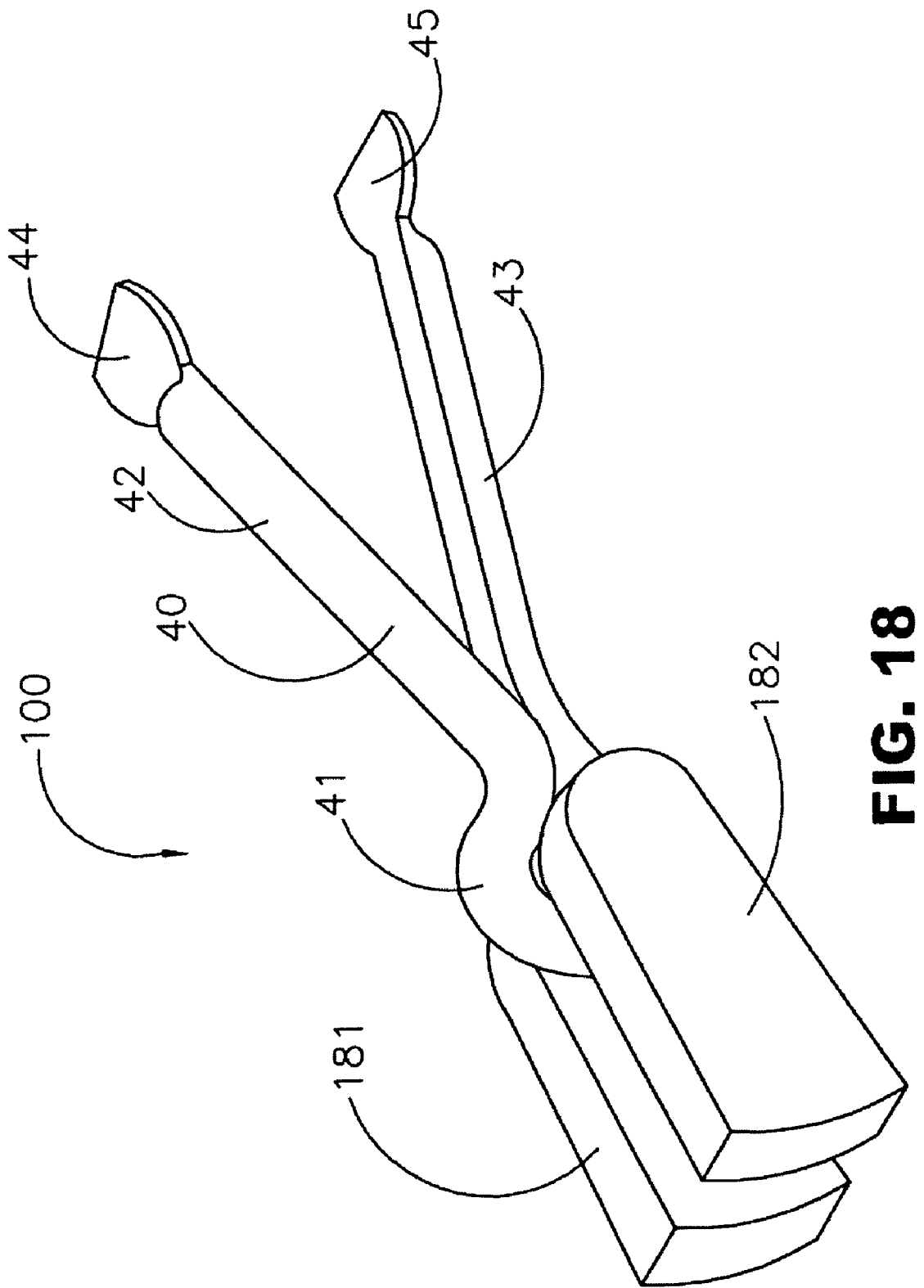
FIG. 18 depicts the clip remover and clip of FIG. 17 wherein the clip remover is engaged.

Referring now to FIGS. 17 and 18, an embodiment of the invention includes an instrument and method for removing and manipulating the clips 40 described above. A remover instrument 100 comprises first and second clip remover jaws 181, 182, which are shown on either side of the torsion spring coil 41 of a clip 40 in its closed or occluding condition. The first remover jaw 181 has an engagement member 183 extending laterally from its proximal end. The engagement member is generally frusto-conical and is sized and tapered such that it will fit part way into the interior space 49 of the torsion spring coil 41, contacting the inside surface approximately midway between the face 185 of the first engagement member 183 and the jaw 181. Inward movement of the second clip remover jaw 182 forces engagement member 183 into the interior space 49 of the torsion spring coil 41.

The remover jaws 181, 182 may be attached to any suitable grasping mechanism that allows the remover jaws 181, 182 to be manipulated so as to selectively engage and disengage the engagement members 183. When the engaging member is made to engage within the interior space of the torsion spring coil 41 of a clip 40, the engaging member 183 comes into contact with the torsion spring coil 41. The tapered engaging member 183 forces the torsion spring coil 41 to become larger, thus opening the clip 40 as shown in FIG. 18. This allows the clip 40 to be removed from any tissue that was occluded by the clip 40.

In some embodiments of the invention, the follower may be formed from an elongate planar member bent to a desired shape. FIG. 20 is a side view of an exemplary version of such a follower 200 that provides the additional benefit of preventing inadvertent proximal movement of the clips 40 in the clip holder 71. The distal end of the follower 200 is divided into four portions 201, 202, 203, 204 that are bent to form an S-shape. The upper-most portion of the follower 200 is the clip push engagement portion 201 which has a distal end 209 that is configured for engagement by the clip push fingers 51. The follower 200 is shaped so that when the follower is positioned in the clip holder 72, the clip engagement portion 201 is above the clip holder rails 72 and the outer edges of the lower surface 207 of the clip engagement portion 201 engage and slide along the clip holder rails 72. The S-shape of the follower 200 positions the third follower portion 203 below the clip holder rails 72 when the follower 200 is installed in the clip holder 72. The outer edges of the upper surface 208 of the third follower portion 203 engage and slide along the lower surface of the clip holder rails 72. The first and third follower portions 201, 203 are connected by the second follower portion 202, which is narrowed so that it will pass between the clip holder rails 72.

The follower 200 has a long tail section formed by three straight follower portions 204, 205, 206. This tail section extends distally from the S-shaped forward section of the follower 200. The tail section is bent downward to provide a biasing and movement resisting force when the follower 200 is installed in the clip holder. The follower 200 has a first straight section 204 that is substantially horizontal. This is connected to a second straight section 205 that is angled slightly downward. The straight section 205 connects to long tail section 206 that is angled downward even further. The tail section 206 is configured to contact the bottom of the clip holder 71 to provide friction against proximal movement of the clip stack during reset of clip pusher 50. Sections 205, 206 also provide a spring force between the follower 200 and clip holder 71.

Figure 21:
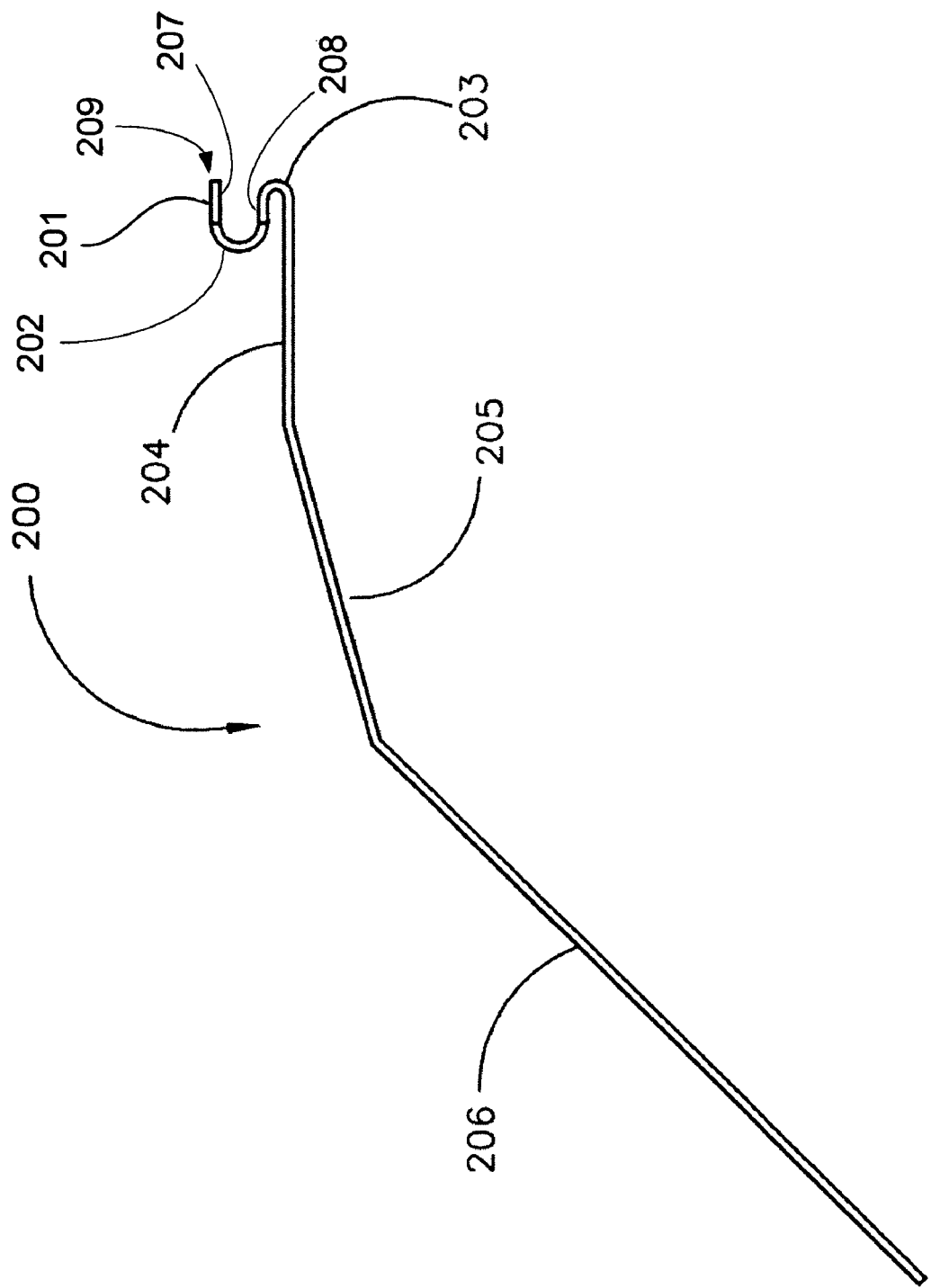
FIG. 21 is a side view of a follower that may be used in applicators according to embodiments of the invention.
Figure 22:
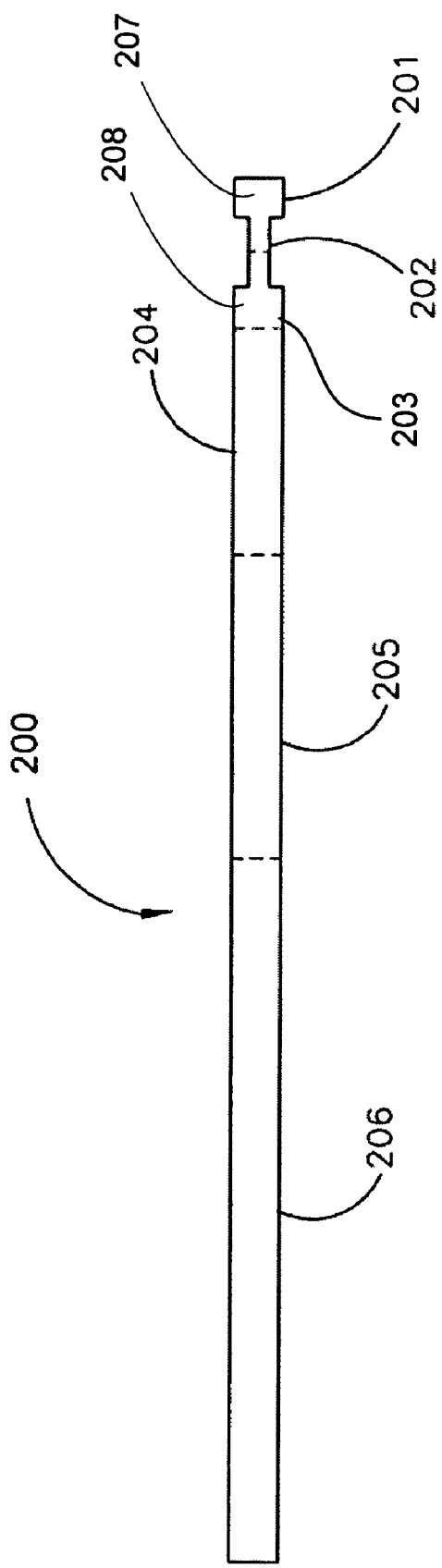
FIG. 22 is a plan view of a sheet member used to produce the follower of FIG. 21.

The follower 200 may be formed from any suitable bendable but resilient material, such as a thin metal sheet. FIG. 21 shows a sheet metal layout of the elongate member used to form the follower 200 prior to its being bent into the form shown in FIG. 20.

It is desirable that a significant force exists between the upper and lower occlusion members 42, 43 at and near the closed position. Some mesentery arteries and veins, for example, are quite small but often require occlusion. Clips that exhibit little or no preload force (i.e., force in the closed position) cannot adequately occlude such vessels. Winding torsion spring coil 41 around a dowel and transitioning the ends of the torsion spring coil 41 into occlusion arms 42, 43 will result in little or no preload. However, a significant preload can be imparted by a variety of mechanical means such as distorting torsion coil 41 so as to establish a teardrop shape such as that shown in FIG. 3. The preload force imparted into the occlusion section 40 is offset by the force caused by the additional stress stored in the torsion coil 41.

In an alternative approach, the occlusion members 42, 43 can be twisted or distorted slightly out of line so that the occlusion members 42, 43 are no longer coplanar and can be rotated passed one another. For some embodiments and uses, the torsion coil 41 may be adequately pre-stressed by rotating the occlusion members 42, 43 passed one another by at least 20 degrees, then returning the occlusion members 42, 43 to a near parallel state and re-twisting the occlusion members 42, 43 so that they lie over and engage one another as shown in FIG. 3. This process stores a substantial preload force between occlusion members 42, 43, which is again offset by torsion spring forces arising from the additional stress in the torsion spring coil 41.

Yet another alternative is to form the coil 41 so as to be open at the transition points to the occlusion members 42, 43 but with the distal ends of members 42, 43 touching. Applying radial forces to the top and bottom of the coil 41 while holding the distal ends of occlusion members 42 and 43 together then closes the opening in the coil 41, engendering a preload between occlusion members 42, 43.

Because implantable grade titanium alloy, Ti-6A1-4V ELI, is generally delivered in an annealed state, the preload force can be further increased by heat treatment. In one embodiment, the formed clip is heated to a temperature just below the transition temperature (1725 degrees Fahrenheit for example) for fifteen minutes in a vacuum oven, purged with argon until the sample is cooled, reheated to 900 degrees Fahrenheit for four hours, and purged with argon until cool. A certain amount of reforming may be required owing to heat distortion. The temperature, heating time and environment can be varied to yield varying preload forces.

As previously noted, the applicator 10 is especially constructed for use in laparoscopic surgery wherein the applicator 10 must be inserted through as small an opening as possible in the patient's body although it can be readily used for open procedures.

It will be appreciated that a method of operating the applicator 10 may include:
  Loading a plurality of occlusion spring clips 40 in the clip holder 71;
  Compressing trigger 12 until jaws 15 and 16 are just closed;
  Inserting jaw actuator tube 14 into a cannula;
  Releasing trigger 12 such that the jaw actuator tube 14 resets to the initial state;
  Maneuvering the jaws 15, 16 to place tissue 49 therebetween; and
  Compressing trigger 12 until clip 40 is forced out of the clip holder and over the jaws 15, 16 to be ejected through the jaw slot 91 and cut-out 92.

It will be understood that the clips 40 may be loaded into the clip holder 71 without consideration to any up or down clip orientation since the clips are symmetric in that regard. Either clip guide 44, 45 can be oriented toward clip push rod 50. This symmetry eliminates orientation mistakes in the manufacturing process.

Thus, it is seen that the applicator 10, clip 40 and methods of the invention readily achieve the objectives and advantages delineated above as well as those inherent therein. While certain preferred embodiments of the invention have been illustrated and described for purposes of the present disclosure, numerous changes in the arrangement and construction of parts and steps may be made by those skilled in the art, which changes are encompassed within the scope and spirit of the present invention.

Many embodiments and adaptations of the present invention other than those herein described, will be apparent to those skilled in the art by the foregoing description thereof, without departing from the substance or scope of the invention. While the present invention has been described herein in detail in relation to its exemplary embodiments, it is to be understood that this disclosure is only illustrative and exemplary of the present invention. Accordingly, the foregoing disclosure is not intended to limit the scope of the present invention which is defined by the claims and their equivalents.

What is claimed is:

1. An occlusion clip comprising:
  an occlusion portion having
    an upper single element occlusion member having proximal and distal upper member ends;
    a lower single element occlusion member having proximal and distal lower member ends, the lower single element occlusion member and the upper single element occlusion member combining to define an occlusion member plane;

a spring portion having
a torsion spring connecting the proximal upper member end to the proximal lower member end, the torsion spring having a spring height dimension in the occlusion member plane perpendicular to the upper and lower single occlusion members and being adapted to bias the upper and lower single element occlusion members toward a closed position wherein the upper single element occlusion member is in force contact with the lower single element occlusion member;

a clip guide portion having
an upper clip guide extending from the distal upper member end, the upper clip guide including a first planar member having a top upper guide surface and an engaging bottom upper guide surface, the first planar member being perpendicular to the occlusion member plane when the upper and lower single occlusion members are in engagement; and a lower clip guide extending from the distal lower member end, the lower clip guide including a second planar member having a bottom lower guide surface and an engaging top lower guide surface, the second planar member being parallel to the first planar member when the upper and lower single occlusion members are in engagement;

wherein:
the occlusion portion and the spring portion are formed from wire having a wire width, and the occlusion portion and the spring portion are each no wider, perpendicular to the occlusion member plane, than the wire width; and
the clip guide portion is wider than the wire width.

2. An occlusion clip according to claim 1 wherein the spring height dimension increases as a rotational separation between the single element upper occlusion member and the single element lower occlusion member increases.

3. An occlusion clip according to claim 1 wherein the upper and lower single element occlusion members and the torsion spring are formed from a single continuous wire segment having first and second wire ends.

4. An occlusion clip according to claim 3 wherein the wire segment is formed from titanium and has a diameter in a range from about 10 mils to about 50 mils.

5. An occlusion clip according to claim 3 wherein the wire segment is formed from titanium and has a diameter in a range from about 20 mils to about 40 mils.

6. An occlusion clip according to claim 1 wherein the torsion spring biases the upper and lower single occlusion members to exert an occluding force of at least 0.20 pounds.

7. An occlusion clip according to claim 1 wherein the widths of the occlusion portion and the spring portion are each in a range from about 10 mils to about 50 mils.

8. An occlusion clip according to claim 7 wherein the widths of the occlusion portion and the spring portion are each in a range from about 20 mils to about 40 mils.

9. An occlusion clip according to claim 3, wherein the wire has a height, and the occlusion portion has a maximum occlusion height dimension in the occlusion member plane that is no greater than twice the wire height.

10. An occlusion clip according to claim 9 wherein the wire segment is formed from titanium and has a diameter in a range from about 10 mils to about 40 mils.

11. An occlusion clip according to claim 9 wherein the wire segment is formed from titanium and has a diameter in a range from about 15 mils to about 30 mils.

12. An occlusion clip according to claim 9 wherein the torsion spring defines a maximum interior height dimension in the occlusion plane when the upper and lower single occlusion members are in engagement, the maximum interior height dimension being less than twice the wire height.

13. An occlusion clip according to claim 9 wherein the torsion spring biases the upper and lower single occlusion members to exert an occluding force of at least 0.20 pounds.

14. An occlusion clip according to claim 1, wherein the upper clip guide has a width greater than a width of the upper single occlusion member, and the lower clip guide has a width greater than a width of the lower single occlusion member.

15. An occlusion clip comprising a single continuous wire segment having a wire width and first and second wire ends and being so formed as to have a wire loop, an upper leg extending from an upper portion of the wire loop to the first wire end, and a lower leg extending from a lower portion of the wire loop to the second wire end, wherein:

all bends in the wire segment to form the wire loop and the upper and lower legs occur in only one plane;

the upper portion of the wire loop so overlies the lower portion of the wire loop that the wire loop as a whole has a width no greater than the wire width;

each of the upper leg and the lower leg comprises:

a distal portion having a clip guide portion provided proximate the respective first or second wire end, the clip guide portion comprising a planar member having an engagement surface; and a proximal portion having an occlusion portion extending from the wire loop to the respective clip guide portion, the occlusion portion comprising an inner engaging surface;

wherein the engagement surfaces of the planar members extend from the occlusion portions to the wire ends; and wherein the engagement surfaces of the planar members are parallel to one another and coplanar with the inner engaging surfaces of the occlusion portions when the occlusion portions are in engagement;

the occlusion portions collectively define an occlusion region of the occlusion clip;

the occlusion region as a whole has a width no greater than the wire width;

the wire loop biases the occlusion clip to a closed position in which the upper leg occlusion portion contacts the lower leg occlusion portion;

the bias creates a clamping force between the upper leg occlusion portion and the lower leg occlusion portion, in the closed position, sufficient to occlude a vessel or duct intervening between the occlusion portions; and each clip guide portion has a width that is greater than the wire width.

16. The occlusion clip of claim 15, wherein each clip guide portion tapers in height distally toward the respective first or second wire end.

17. The occlusion clip of claim 15, wherein the clamping force is at least 0.20 pounds.

18. The occlusion clip of claim 15, wherein the clip has mirror-image symmetry with respect to the plane in which the bends occurs.

19. The occlusion clip of claim 15, wherein the clip has mirror-image symmetry with respect to a plane that is perpendicular to the plane in which the bends occur and that divides the clip into upper and lower halves.

20. The occlusion clip of claim 19, wherein the clip has mirror-image symmetry with respect to the plane in which the bends occurs.

21. The occlusion clip of claim 15, wherein the clip is formed from a material comprising titanium.

22. The occlusion clip of claim 15, wherein the clip is formed from a titanium alloy.

23. The occlusion clip of claim 22, wherein the titanium alloy comprises Ti-6A1-4V ELI.

* * * * *